United States Patent [19]
Alker et al.

[11] Patent Number: 5,358,953
[45] Date of Patent: Oct. 25, 1994

[54] IMIDAZOPYRIDINE PAF/$H_1$ ANTAGONISTS

[75] Inventors: David Alker; Robert J. Bass, both of Sandwich, United Kingdom; Kelvin Cooper, Groton, Conn.

[73] Assignee: Pfizer Inc., New York, N.Y.

[21] Appl. No.: 87,736

[22] PCT Filed: Jan. 24, 1992

[86] PCT No.: PCT/EP92/00163
§ 371 Date: Jul. 12, 1993
§ 102(e) Date: Jul. 12, 1993

[87] PCT Pub. No.: WO92/14734
PCT Pub. Date: Sep. 3, 1992

[30] Foreign Application Priority Data
Feb. 13, 1991 [GB] United Kingdom ................ 9102997

[51] Int. Cl.⁵ ............... A61K 31/435; C07D 471/04; C07D 235/00; C07D 519/00
[52] U.S. Cl. .................... 514/290; 514/291; 514/303; 546/80; 546/93; 546/118
[58] Field of Search ............. 546/80, 93, 118; 514/290, 291, 303

[56] References Cited
U.S. PATENT DOCUMENTS 5,114,919  5/1992  Baldwin et al. .................. 514/11
5,250,681 10/1993  Shoji et al. ...................... 546/81

OTHER PUBLICATIONS

Alker et al, CA 118: 22232j (1992).

*Primary Examiner*—Cecilia Tsang
*Attorney, Agent, or Firm*—Peter C. Richardson; Gregg C. Benson; A. Dean Olson

[57] ABSTRACT

Compounds of formula (1), wherein X is CH or N; Z is CH=CH or S; A is $CH_2CH_2$, CH=CH, $CH(OH)CH_2$, or $COCH_2$; B is a direct link or —$CH_2$—, —$CH(CH_3)$— or —$C(CH_3)_2$—; or when Z is CH=CH, B may form a cyclopentane ring fused to the attached benzene ring; Y completes a fused benzo or thienyl ring which is optionally substituted by halo or $C_1$-$C_4$alkyl; n is 0, 1 or 2; and m is 0 or 1; are antagonists of both PAF and histamine $H_1$ having utility in the treatment of allergic inflammatory conditions such as allergic rhinitis.

8 Claims, No Drawings

IMIDAZOPYRIDINE PAF/H₁ ANTAGONISTS

This invention relates to imidazopyridines, specifically to certain 4-substituted-1-(2-methylimidazo[4,5-c]pyrid-1-yl)-benzene and -alkylbenzene derivatives. The compounds possess both histamine (H₁) and platelet activating factor (PAF) antagonist activities and have clinical utility in the treatment of allergic inflammatory conditions of both the respiratory tract, such as allergic rhinitis, sinusitis and asthma, and skin, such as atopic dermatitis and urticaria.

The acute systems of allergic rhinitis, e.g. sneezing, nasal and ocular secretion and itching, are generally well controlled by H₁-antagonists. However, these agents elicit little or no relief of the congestion caused by both by vasodilation and the oedema due to increased vascular permeability. Furthermore, H₁-antagonists do not affect the accumulation of inflammatory cells which contribute to both the delayed response and the hyper responsiveness to allergen in chronic disease. The potent oedemogenic activity of PAF together with its known release from and activation of many types of inflammatory features of allergic rhinitis. The compounds of the invention are both PAF and H₁-antagonists and thus have the potential to ameliorate all the major symptoms of chronic allergic rhinitis.

In addition, while histamine contributes to the acute bronchoconstriction to allergen in asthma, it has little effect on either the delayed bronchoconstrictor responses or the non-specific bronchial hyperresponsiveness associated with the accumulation of inflammatory cells in the lower airways. The involvement of PAF in this inflammatory response, together with its bronchoconstrictor activity, supports the potential role for a dual PAF/H₁ antagonist in the treatment of asthma. Similarly, a dual PAF/H₁ antagonist would be expected to be superior to antihistamines alone for the treatment of allergic cutaneous diseases, such as atopic dermatitis and urticaria, since, while antihistamines reduce itching and reddening, they are less effective against the wheal response associated with the influx of inflammatory cells. The compounds of the invention would also be expected to be of value in the treatment of other conditions in which pathophysiological changes are mediated both by histamine as well as histamine-independent inflammatory events.

In our European patent application no 0310386 we disclose a series of dihydropyridine PAF antagonists wherein the 2-position substituent includes in particular a (2-methylimidazo[4,5-c]pyrid-1-yl)phenyl group. U.S. Pat. No. 3,326,924 discloses certain aza-dibenzocycloheptenes as antihistamines including 3-aza-5-(4-piperidylidene)-10,11-dihydro-5H-dibenzo[a,d]-cycloheptene and its 4-aza analogue (5,6-dihydro-11-(4-piperidylidene)-11H-benzo[5,6]cyclohepta[1,2-b]pyridine) as well as 7 and 8-chloro and 7,8 and 9-methyl derivatives thereof.

According to the present invention there are provided compounds having the general formula:

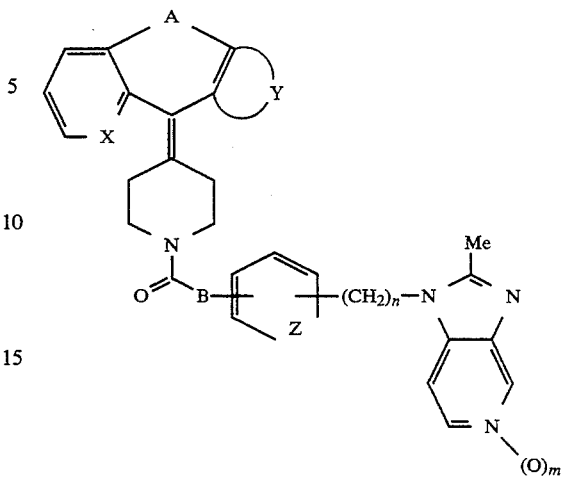

(I)

and pharmaceutically acceptable salts thereof wherein:
X is CH or N;
Z is CH=CH or S;
A is $CH_2CH_2$, CH=CH, $CH(OH)CH_2$, or $COCH_2$;
B is a direct link or $-CH_2-$, $-CH(CH_3)-$ or $-C(CH_3)_2-$, or when Z is CH=CH, B may form a cyclopentane ring fused to the attached benzene ring;
Y completes a fused ring which is

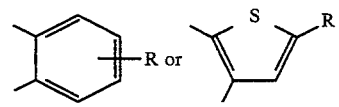

wherein R is H, halo or $C_1$-$C_4$ alkyl;
n is 0, 1 or 2;
and m is 0 or 1.

In the above definition, the term halo means fluoro, chloro, bromo or iodo; alkyl and alkoxy group of 3 or more carbon atoms may be straight or branched-chain, and the linking group A may be attached in either sense when it is asymmetric. When the compounds contain asymmetric centres the compounds can exist as enantiomers and diastereoisomers. Such isomers may be separable by physical methods, e.g. by fractional crystallisation or chromatography of the parent compounds or of a suitable salt or derivatives thereof. The invention includes all the enantiomers whether separated or not.

The pharmaceutically acceptable acid addition salts of the compounds of the formula (I) which form such salts are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts.

In preferred embodiments of the invention, X is N, Z is CH=CH and Y completes a benzo-fused ring of formula:

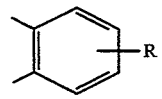

particularly when R is H or Cl. B is preferably a direct link or $CH_2$ and n is 0 and m is 0. Particularly preferred are compounds wherein R is Cl, B is direct link, A is $CH_2CH_2$, n is 0 and m is 0.

The compound 4-(8-chloro-5,6-dihydro-11H-benzo[5,6]cyclohepta[1,2-b]-pyrid-11-ylidene)-1-[4-(2-methylimidazo[4,5-c]pyrid-1-yl)-benzoyl]piperidine is especially preferred.

The compounds of the invention wherein m is 0 may be prepared by the following route which involves reaction of a piperidine derivative of formula (II) with an acid (or activated derivative thereof) of formula (III).

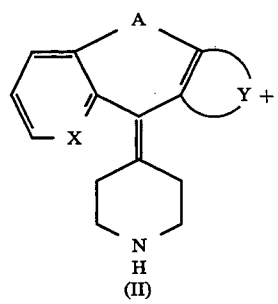

(II)

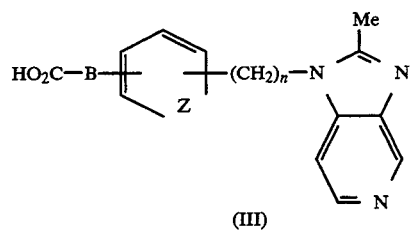

(III)

The reaction of the compounds of formula (II) and (III) is achieved using conventional amide coupling techniques. Thus in one process the reaction is achieved with the reactants dissolved in an organic solvent, e.g. dichloromethane, using a diimide condensing agent, for example 3-(dimethylaminopropyl)-1-ethylcarbodiimide, or N,N'-dicyclohexylacarbodiimide, advantageously in the presence of 1-hydroxybenzotriazole and an organic base such as N-methylmorpholine. The reaction is generally complete after a period of from 2 to 24 hours at room temperature and the product is then isolated by conventional procedures, i.e. by washing with water, or filtration, to remove the urea byproduct and evaporation of the solvent. The product may be further purified by crystallisation or chromatography if necessary.

A number of subsequent transformation reactions are possible. Thus reduction of the product wherein A is $COCH_2$, for example with sodium borohydride, yields the corresponding compound wherein A is $CH(OH)CH_2$. N-oxides (wherein m is 1) is prepared by oxidation of the corresponding imidazopyridine (m=0) using, for example, 3-chloroperbenzoic acid.

The starting materials of formula (II) are prepared by literature methods following the procedures described by Engelhardt et al in J. Med. Chem., 1965, 8, 829; by Waldvogel et al in Helvetica Chimica Acta, 1976, 59, 886 and in U.S. Pat. No. 3,326,924. The starting materials of formula (III) are prepared following the procedures as described in European patent 0310386 and as described in the preparations given hereinafter.

The activity of the compounds of the invention as $H_1$ antagonists is shown by their ability to inhibit histamine-induced contraction of guinea pig trachea in vitro. Testing is performed as follows:

Spirally-cut guinea pig trachea strips are suspended under tension (2 g) in tissue baths containing 15 ml of continuously gassed (95% $O_2$, 5% $CO_2$) Krebs buffer (118 mM NaCl, 4.62 mM KCl, 1.16 mM $MgSO_4$, 1.18 mM $KH_2PO_4$, 25 mM $NaHCO_3$, 11 mM glucose, 2.5 mM $CaCl_2$) containing indomethacin (2 μM). Following an equilibration period of 45 minutes, histamine dihydrochloride is added to the tissue bath, to a final concentration of $10^{-5}$ M, and the resulting contraction recorded isometrically. Following contraction for 30 minutes, the tissue is washed with buffer until fully relaxed to baseline. This is followed by a further histamine contraction (30 minutes) and wash. Tissues are contracted with histamine for a third time but not washed. Following 30 minutes sustained contraction the first dose of test compound is added to the tissue bath and effects recorded for 20 minutes. Increasing cumulative doses of compound are added every 20 minutes and the effects quantified. An $IC_{50}$ value is calculated as the concentration of the compound required a relax the third sustained histaime contraction by 50 percent.

The activity of the compounds of the invention as PAF antagonists is shown by their ability to inhibit the platelet aggregating activity of PAF in vitro. Testing is performed as follows:

Blood samples are taken from a rabbit into 0.1 vol (77 mM) disodium ethylenediamine tetraacetic acid and the samples centrifuged at 150 ×g for 15 minutes to obtain platelet rich plasma. The plasma is further centrifuged at 2000× g for 10 minutes to give a platelet pellet which is washed with a buffer solution (4 mM $KH_2PO_4$, 6 mM $Na_2HPO_4$, 100 mM NaCl, 5 mM glucose and 0.1% bovine serum albumin, pH 7.25) and finally resuspended in buffer solution to a concentration of $2\times10^8$ platelets/ml. The washed platelets are pre-incubated with stirring for 2 minutes at 37° C. in an aggregometer in the presence of an ADP scavenging system (1 mM creatinine phosphate, 27 U/ml creatinine phosphokinase and 10 mM $MgCl_2$), 1 mM $CaCl_2$ and either vehicle alone (dimethylsulphoxide) or vehicle containing the particular compound under test. $C_{18}$-PAF is added at a sufficient concentration to give a maximum aggregating response in the absence of test compound ($10^{-8}$ to $10^{-9}$M), and the platelet aggregation is measured by following the increase in light transmission of the solution. The experiment is repeated in the presence of a range of concentrations of the test compound and the concentration of compound required to reduce the response to 50% of its maximum value is recorded as the $IC_{50}$ value.

The activity of the compounds of formula (I) as dual PAF and $H_1$ antagonists is demonstrated in vivo by their ability to inhibit increases in cutaneous vascular permeability induced by intradermal injections of PAF or histamine in mice. Animals are dosed orally or intravenously with test compound. Forty five minutes (for oral) or 10 minutes (for i.v.) after dosing, each animal is given a single intradermal injection of either histamine (13.5 nmoles) of PAF (30 pmoles) on its dorsal side, directly behind the head. Immediately following the injection, Evans Blue dye (250 μl, 6.25 mg/ml) is injected intravenously. After thirty minutes the animals are killed with a lethal injection of pentobarbitone, the dorsal skin removed, and areas of intradermal blueing punched out. The extent of blueing is measured by extracting the dye from the skin punches with formamide for 24 hours at 70° C. and recording absorption at 620 nm in a spectrophotometer. The $ID_{50}$ is calculated as the dose of compound which reduces absorbance (blueing) by 50% compared to untreated controls.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either along or in admixture with excipients, or in the form of elixiers or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of allergic and inflammatory conditions, oral dosages of the compounds will generally be in the range of from 2–1000 mg daily for an average adult patient (70 kg). Thus for a typical adult patient, individual tablets or capsules will contain from 1 to 500 mg of active compound, in a suitable pharmaceutically acceptable vehicle or carrier. Dosages for intravenous administration would typically be within the range 1 to 10 mg per single dose as required. For the treatment of allergic asthma and rhinitis, intranasal administration or inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus in a further aspect, the invention provides a pharmaceutical composition comprising a compound of the formula (I), or a pharmaceutically acceptable diluent or carrier.

The invention also includes a compound of the formula (I), or a pharmaceutically acceptable salt thereof, for use in medicine, in particular in the treatment of allergic and inflammatory conditions in a human being.

The preparation of the compounds of formula (I) will now be more particularly illustrated by reference to the following experimental Examples. The purity of compounds was routinely monitored by thin layer chromatography using Merck Kieselgel 60 $F_{254}$ plates. $^1$H-Nuclear magnetic reasonance spectra were recorded using either a Nicolet QE-300 or a Bruker AC-300 spectrometer and were in all cases consistent with the proposed structures. Chemical shifts are given in parts-per-million downfield from tetramethylsilane using conventional abbreviations for designation of major peaks; s, singlet; d, doublet; t, triplet; m, multiplet and br, broad.

EXAMPLE 1

4-(8-Chloro-5,6-dihydro-11H-benzo[5,6]cyclohepta[1,2-b]pyrid-11-ylidene)-1-[4-(2-methylimidazo[4,5-c]pyrid-1-yl)benzoyl]piperidine hemihydrate A solution of 4-(8-chloro-5,6-dihydro-11-H-benzo[5,6]cyclohepta[1,2-b]pyrid-11-ylidene-piperidine (224 mg, 0.75 mmol) and (4-(2-methylimidazo[4,5-c]pyrid-1-yl)benzoic acid (190 mg, 0.75 mmol) in dichloromethane (12 ml) was treated sequentially with 1-hydroxybenzotriazole hydrate (102 mg, 0.75 mmol), 1-(3-dimethylaminopropyl)-3-ethylcarbodiimide hydrochloride (290 mg, 1.5 mmol) and 4-methylmorpholine (165 μl; 1.5 mmol). The mixture was stirred at room temperature for 16 hours, washed with water, dried over magnesium sulphate and evaporated. The residue was purified by chromatography on silica using dichloromethane plus 3–4% methanol as eluant. Appropriate fractions were combined and evaporated to give the title compound (113 mg, 27%) as a colourless foam which was characterised as a hemihydrate. Found: C,71.1; H,5.2; N,12.3. $C_{33}H_{28}ClN_5O$. 0.5 $H_2O$ requires C,71.4; H,5.3; N,12.6%.

EXAMPLES 2–6

The following Examples were prepared by reacting 4-(8-chloro-5,6-dihydro-11H-benzo[5,6]cyclohepta(1,2-b]pyrid-11-ylidene)piperidine with the appropriate acid using the method described in Example 1 and were characterised in the form indicated.

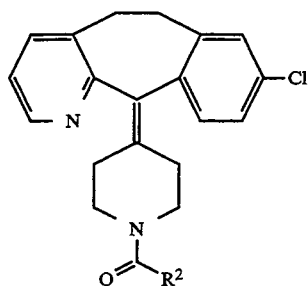

| Example No | R² | Form characterised | Analysis (%) (Theoretical in brackets) | | |
|---|---|---|---|---|---|
| | | | C | H | N |
| 2 | [2-methyl-1-(methylindan-5-yl)imidazo[4,5-c]pyrid-1-yl] | foam, hemihydrate | 72.8 (72.6 | 5.7 5.6 | 11.7 11.8) |
| 3 | [4-methylbenzyl-N-(2-methylimidazo[4,5-c]pyrid-1-yl)] -CH₂-N group | foam, hemihydrate | 71.9 (71.7 | 5.4 5.5 | 12.0 12.3) |
| 4 | -CH₂-phenyl-N(2-methylimidazo[4,5-c]pyrid-1-yl) | foam, hemihydrate | 71.9 (71.7 | 5.6 5.5 | 12.3 12.3) |
| 5 | (3-methylphenyl)-2-methylimidazo[4,5-c]pyrid-1-yl | foam, 0.25 EtOAc | 72.0 (71.9 | 5.3 5.1 | 12.3 12.6) |
| 6 | (2-methylphenyl)-2-methylimidazo[4,5-c]pyrid-1-yl | foam, 0.25 EtOAc | 71.5 (71.9 | 5.5 5.1 | 12.4 12.6) |

EXAMPLE 7

4-(5H-Dibenzo[a,d]cycloheptene-5-ylidene)-1-[4-(2-methylimidazo[4,5-c]pyrid-1-yl) benzoyl piperidine hemihydrate This was prepared as described in Example 1 using 4-(5H-dibenzo[a,d]cyclohepten-5-ylidene)piperidine hydrochloride (see J. Med. Chem., 1965, 8, 829) instead of 4-(8-chloro-5,6-dihydro-11H-benzo[5,6]cyclohepta[1,2-b]pyridin-11-ylidene)piperidine. The title compound was obtained as a colourless foam and was characterised as a hemihydrate. Found: C,78.9; H,5.6; N,11.0. $C_{34}H_{28}N_4O$. 0.5 $H_2O$ requires C,78.9; H,5.8; N,10.8%.

EXAMPLE 8

1-[4(2-Methylimidazo[4,5-c]pyrid-1-yl)benzoyl]-4-(10-oxo-9,10-dihydro-4H-benzo[4,5]cyclohepta[1,2-b]thiophen-4-ylidene)piperidine This was prepared as described in Example 1 using 4-(10-oxo-9,10-dihydro-4H-benzo[4,5]cyclohepta[1,2-b]thiophen-4-ylidene)piperidine (see Helv. Chim. Acta, 1976, 59, 886) instead of 4-(8-chloro-5,6-dihydro-11H-benzo[5,6]cyclohepta[1,2-b]pyrid-11-ylidene)piperidine. The title compound was obtained as a colourless foam which was characterised as a monohydrate. Found: C,70.1; H,5.1; N,10.1. $C_{32}H_{26}N_4O_2S$. $H_2O$ requires C,70.0; H,5.1; N,10.2%.

EXAMPLE 9

4-(8-Chloro-5,6-dihydro-11H-benzo[5,6]cyclohepta[1,2-b]pyrid-11-ylidene)-1-[4-(2-methylimidazo[4,5-c]pyrid-1-yl-5-oxide)benzoyl]piperidine A solution of 3-chloroperbenzoic acid (50%; 126 mg, 0.37 mmol) in dichloromethane (3 ml) was added dropwise over 10 minutes to a stirred, ice-cooled solution of 4-(8-chloro-5,6-dihydro-11H-benzo[5,6]cyclohepta[1,2-b]pyrid-11-ylidene)-1-[4-(2-methylimidazo[4,5-c]pyrid-1-yl)benzoyl]piperidine hemihydrate (200 mg, 0.37 mmol) (Example 1). The mixture was stirred at 0° C. for 19 hours, treated with a further portion of 3-chloroperbenzoic acid (25 mg), stirred with ice-cooling for a further 25 hours, washed with saturated aqueous sodium hydrogen carbonate solution and water, dried over magnesium sulphate and evaporated. The residue was purified by chromatography on silica using dichloromethane plus 5% methanol plus 0.1–0.5% saturated aqueous ammonia solution as eluant. Appropriate fractions were combined and evaporated to give the title compound (44 mg, 21%) as a colourless glass, m.p. 176°–180° C., which was characterised by its $^1$H-NMR spectrum. $^1$H-NMR (CDCl$_3$) δ=9.03(1H,s), 8.39(1H,d,J=8 Hz), 8.04(1H,s), 7.64(2H,d,J=8 Hz), 7.37(2H,d,J=8 Hz), 6.95–7.25(6H,m), 3.25–4.15(4H,m), 1.7—3.0(8H,m).

EXAMPLE 10

4-(10-Hydroxy-9,10-dihydro-4H-benzo[4,5]cyclohepta[1,2-b]thiophen-4-ylidene)-1-[4-(2-methylimidazo[4,5-c]pyrid-1-yl]benzoyl]piperidine A solution of 1-[4-(2-methylimidazo[4,5-c]pyrid-1-yl)benzoyl]-4-(10-oxo-9,10-dihydro -4H-benzo[4,5]cyclohepta[1,2-b]thiophen-4-ylidene)piperidine (200 mg, 0.38 mmol) (Example 8) and sodium borohydride (200 mg) in methanol (20 ml) was stirred at room temperature for 4 hours and evaporated. The residue was partitioned between dichloromethane and water and the organic layer was washed with water, dried over magnesium sulphate and evaporated. The residue was triturated with hexane to give the title compound (70 mg, 35%) as a colourless foam which was characterised as a dihydrate. Found: C,67.9; H,5.4; N,9.6. $C_{32}H_{28}N_4O_2S$. 2 $H_2O$ requires C,67.5; H,5.6; N,9.9%.

EXAMPLE 11

4-(8-Chloro-5,6-dihydro-6-oxo-11H-benzo[5,6]cyclohepta[1,2-b]-pyrid-11-ylidene)-1-[4-(2-methylimidazo[4,5-c]pyrid-1-yl)benzoyl]piperidine This was prepared as described in Example 1 using 4-(8-chloro-5,6-dihydro-6-oxo-11H-benzo[5,6]cyclohepta[1,2-b]pyrid-11-ylidene)piperidine (see J. Org. Chem., 1990, 55, 3341) instead of 4-(8-chloro-5,6-dihydro-11-benzo[5,6]cyclohepta[1,2-b]pyrid-11-ylidene)-piperidine. The title compound was obtained as a colourless gum which was characterised containing 1.5 equivalents of water. Found: C,67.2; H,5.2; N,11.4. $C_{33}H_{26}ClN_5O_2$. 1.5 $H_2O$ requires C,67.0; H,4.9; N,11.9%.

EXAMPLE 12

4-(10,11-Dihydro-5H-dibenzo[a,d]cyclohepten-5-ylidene)-1-[4-(2-methylimidazo[4,5-c]pyrid-1-yl)benzoyl]piperidine This was prepared as described in Example 1 using 4-(10,11-Dihydro-5H-dibenzo[a,d]cyclohepten-5-ylidene)piperidine (see EP-A-0347123, 1989) instead of 4-(8-chloro-5,6-dihydro-11H-benzo[5,6cyclohepta[1,2-b]pyridin-11-ylidene)piperidine. The title compound was obtained as a colourless foam (248 mg, 48%) which was characterised as a hemihydrate. Found: C,78.4; H,5.9; N,10.7. $C_{34}H_{30}N_4O$. 0.5 $H_2O$ requires C,78.5; H,6.0; N,10.8%.

EXAMPLE 13

4-(8-Chloro-11-H-benzo[5,6]cyclohepta[1,2-b]pyrid-11-ylidene)-1-[4-(2-methylimidazo[4,5-c]pyrid-1-yl)benzoyl]piperidine This was prepared as described in Example 1 using 4-(8-Chloro-11-H-benzo[5,6]cyclohepta[1,2-b]pyrid-11-ylidene)piperidine (see WO 88/03138, 1988) instead of 4-(8-chloro-5,6-dihydro-11H-benzo[5,6]cyclohepta[1,2-b]pyrid-11-ylidene)piperidine. The title compound was obtained as a colourless gum, Rf 0.25 (silica, solvent system: CH$_2$Cl$_2$,CH$_3$OH,NH$_4$OH; 98:7:1), which was characterised by its mass spectrum. M/e, M+ =543 ($C_{33}H_{26}ClN_5O$).

EXAMPLE 14

4-(5,6-Dihydro-11H-benzo[5,6]cyclohepta[1,2-b]pyrid-11-ylidene-1-[4-(2-methylimidazo[4,5-c]pyrid-1-yl)benzoyl]piperidine This was prepared as described in Example 1 using 4-(5,6-Dihydro-11H-benzo[5,6]cyclohepta[1,2-b]pyrid-11-ylidene)piperidine (see J. Med. Chem. 1972, 15, 750) instead of 4-(8-chloro-5,6-dihydro-11H-benzo[5,6]cyclohepta[1,2-b]-pyrid-11-ylidene)piperidine. The title compound was obtained as a beige solid, m.p. 243°–245° C., which was characterised containing 0.67 equivalents of water. Found: C,75.7; H,5.9; N,13.4. $C_{336l}H_{29}N_5O$. 0.67 $H_2O$ requires C,75.7; H,5.8; N,13.4%.

EXAMPLE 15

4-(8-Chloro-5,6-dihydro-6-hydroxy-11H-benzo[5,6]cyclohepta[1,2-b]-pyrid-11-ylidene)-1-[4-(2-methylimidazo[4,5-c]pyrid-1-yl)benzoyl]piperidine This was prepared as described in Example 10 by sodium borohydride4 reduction of 4-(8-Chloro-5,6-dihydro-6-hydroxy-11H-benzo[5,6]cyclohepta[1,2-b]-pyrid-11-ylidene)-1-[4-(2-methylimidazo[4,5-c]pyrid-1-yl)benzoyl]piperidine (see Example 11) The title compound was obtained as a colourless gum, Rf 0.30 (silica, solvent system: CH$_2$Cl$_2$,CH$_3$OH,NH$_4$OH: 93:7:1), which was characterised by its mass spectrum. M/e, M+ =561 ($C_{33}H_{28}ClN_5O_2$).

EXAMPLE 16

4-(8-Chloro-5,6-dihydro-11H-benzo[5,6]cyclohepta[1,2-b]-pyrid-11-ylidene-1-[5-(2-methylimidazo[4,5-c]pyrid-1-yl)-thien-2-oyl]piperidine This was prepared as described in Example 1 using 5-(2-methylimidazo-(4,5-c]pyrid-1-yl)thiophene-2-carboxylic acid (see Preparation 8; 185 mg) instead of 4-(2-methylimidazo[4,5-c]pyrid-1-yl)benzoic acid. The title compound was obtained as a tan coloured foam (121 mg, 38.5%) which was characterised as a sesquihydrate. Found: C,64.3; H,4.8; N,12.0. $C_{31}H_{26}ClN_5OS$. 1.5 $H_2O$ requires C,64.3; H,5.0; N,12.1%.

EXAMPLE 17

4-(8-Methyl-5,6-dihydro-11H-benzo[5,6]cyclohepta[1,2-b]pyrid-11-ylidine)-1-[4-(2-methylimidazo[4,5-c]pyrid-1-yl)benzoyl]piperidine This was prepared as in Example 1 using 4-(8-Methyl-5,6-dihydro-11H-benzo[5,6]cyclohepta[1,2-b]pyrid-11-benzo[5,6]cyclohepta[1,2-b]pyrid-11-ylidene)piperidine (see *J. Med. Chem.* 1991, 34, 457–461; 300 mg) instead of 4-(8-chloro-5,6-dihydro-11-H-benzo[5,6]cyclohepta[1,2-b]pyrid-11-ylidene)piperidine. The title compound was obtained as a glass (270 mg, 49.6%) which was characterised containing 0.25 moles of dichloromethane. Found: C,74.8; H,6.0; N,12.7. $C_{34}H_{31}N_5O$. 0.25 $CH_2Cl_2$ requires C,75.2; H,5.8; N,12.8%.

EXAMPLE 18

4-(8-Chloro-5,6-dihydro-5-oxo-11H-benzo[5,6]cyclohepta[1,2-b]pyrid-11-ylidene)-1-[4-(2-methylimidazo[4,5-c]pyrid-1-yl)benzoyl]piperidine This was prepared as described in Example 1 using 4-(8-chloro-5,6-dihydro-5-oxo-11H-benzo[5,6]cyclohepta[1,2-b]pyrid-11-ylidene-piperidine (see *J. Org. Chem,* 1990, 55, 3341: 80 mg) instead of 4-(8-chloro-5,6-dihydro-11H-benzo[5,6]cyclohepta[1,2-]pyrid-11-ylidene) piperidine. The title compound was obtained as a tan coloured foam (60 mg, 43.5%. Rf 0.08 (silica; solvent system: $CH_3CO_2C_2H_5$, $CH_3OH$, $NH_4OH$; 80:20:1). m/e, M+ =559 ($C_{33}H_{26}ClN_5O_2$).

EXAMPLE 19

4-(8-Chloro-5,6-dihydro-5-hydroxy-11H-benzo[5,6]cyclohepta[1,2-b]pyrid-11-ylidene)-1-[4-(2-methylimidazo[4,5-c]pyrid-1-yl)benzoyl]piperidine This was prepared as described in Example 10 by sodium borohydride reduction of 4-(8-chloro-5,6-dihydro-5-oxo-11H-benzo[5,6]cyclohepta[1,2-b]pyrid-11-ylidene)-1-[4-(2-methyimidazo[4,5-c]pyrid-1-yl)benzoyl]piperidine (from Example 18; 40 mg). The title compound was obtained as a yellow foam (35 mg, 87%) which was characterised as a hydrate containing 0.33 equivalents of ethyl acetate. Found: C,67.7; H,5.2; N,11.4. $C_{33}H_{28}ClN_5O_2$. $H_2O$. 0.33 $C_4H_8O_2$ requires C,67.7; H,5.1; N,11.5%.

PREPARATION 1

4-(2-Methylimidazo[4,5-c]pyrid-1-yl)benzoic acid

A mixture of 4-(2-methylimidazo[4,5-c]pyrid-1-yl)benzonitrile (see EP-0310386) (12.0 g, 51.3 mmol) and sodium hydroxide (22.0 g, 0.55 mmol) in a mixture of ethanol (55 ml) and water (55 ml) was heated under nitrogen at reflux for 1.5 hours, cooled and concentrated under reduced pressure. The brown residue was dissolved in ice-water and glacial acetic acid (33 ml) was added. The resulting precipitate was collected, washed with water and dried under vacuum at 70° C. to give the title compound (9.1 g, 70%) as a buff coloured solid which as characterised by its $^1$H-NMR spectrum. $^1$H NMR (DMSO-d$_6$), 2.50(3H,s), 7.25(1H,d,J=5 Hz), 7.72(2H,d,J=8 Hz), 8.16(2H,d,J=8 Hz), 8.30(1H,d,J=5 Hz), 8.92(1H,s).

PREPARATION 2

Ethyl 4-(2-methylimidazo[4,5-c]pyrid-1-yl)phenyl acetate a) Ethyl 4-aminophenylacetate (17.7 g, 0.1 mole) and sodium hydrogen carbonate (8.4 g, 0.1 mole) were stirred in ethanol (200 ml). 4-Chloro-3-nitropyridine (15.9 g, 0.1 mole) was added as a solution in ethanol (50 ml) and the mixture stirred at room temperature for 3 hours. The mixture was then evaporated to low volume and poured into ethyl acetate (500 ml) and the solution washed with water (200 ml). The organic phase was then extracted with 0.5M hydrochloric acid and the combined aqueous extracts basified with 2M sodium hydroxide and extracted with dichloromethane. The combined organic extracts were dried over was recrystallised from aqueous ethanol to give ethyl 4-(3-nitropyrid-4-ylamino)phenyl acetate (7.32 g), m.p. 124°–126° C. A further 8.56 g was recovered from the mother liquors.

b) The above product (15.7 g) was hydrogenated at 60 p.s.i. (4.1 bar) over 5% palladium on charcoal for 3 hours at room temperature. Filtration and evaporation of the solvent gave ehtyl 4-(3-aminopyrid-4-ylamino)phenyl acetate (14.1 g).

c) Ethyl 4-(3-aminopyrid-4-ylamino)phenyl acetate (14.1 g, 52 mmol), acetic acid (100 ml) and acetic anhydride (100 ml) were mixed and heated at reflux under nitrogen for 1.5 hours. The cooled solution was evaporated to dryness and basified with 10% aqueous sodium carbonate solution then extracted with dichloromethane. The combined organic extracts were evaporated to dryness and purified by chromatography on silica eluting with dichloromethane/ethanol to give ethyl 4-(2-methylimidazo[4,5-c]pyrid-1-yl)phenyl acetate (13.6 g).

PREPARATION 3

4-(2-Methylimidazo[4,5-c]pyrid-1-yl)phenylacetic acid

A solution of ethyl 4-(2-methylimidazo[4,5-c]pyrid-1-yl)phenylacetate (750 mg, 2.54 mmol) and sodium hydroxide 160 mg, 4.0 mmol) in a mixture of ethanol (5 ml) and water (5 ml) was stirred at room temperature for 16 hours and evaporated. The residue was taken up in water, acidified with 2M hydrochloric acid to pH 4–5 and extracted into 1-butanol. The combined 1-butanol extracts were evaporated and the residue triturated with diethyl ether. The resulting solid was collected, washed with hexane and dried to give the title compound (267 mg, 39%) as a buff solid, m.p. 226°–230° C., which was characterised by its $^1$H-NMR spectrum. $^1$H-NMR (d$_6$-DMSO) δ=8.86(1H,s), 8.23(1H,d,J=8 Hz), 7.48(4H,s), 7.15(1H,d,J=8 Hz), 3.70(2H,s), 2.42(3H,s).

PREPARATION 4

4-[(2-Methylimidazo[4,5-c]pyrid-1-yl)methyl]benzoic acid

Ethyl 4-[(2-methylimidazo[4,5-c]pyrid-1-yl)methyl]-benzoate (EP-A-0330327) was hydrolysed following the procedure described in Preparation 3 above to give the title compound as a colourless solid which was used directly in Example 3.

PREPARATION 5

5-(2-Methylimidazo[4,5-c]pyrid-1-yl)indane-2-carboxylic acid (a) Fuming nitric acid (40 ml, 1.5 g/ml) was added dropwise with stirring to acetic anhydride (80 ml ) keeping the temperature of the mixture at 0° C. After the addition was complete 2-cyanoindane (11.33 g, 79.5 mmol), (J. Chem. Soc. (B), (1969), 1197) was added dropwise with stirring over 30 minutes maintaining the reaction temperature between −5° and 0° C. The mixture was stirred for a further 15 minutes then poured onto ice. The mixture was extracted with dichloromethane (4×150 ml) and the extracts were washed with saturated aqueous sodium bicarbonate (3×150 ml), dried over magnesium sulphate and the solvent evaporated under reduced pressure. The residue was recrystallised from ethanol to give 2-cyano-5-nitroindane (12.09 g, 81%) as a yellow solid, m.p. 80°–82° C.

(b) A solution of 2-cyano-5-nitroindane (11.90 g, 63.3 mmol) in methanol/dichloromethane=1:1 (200 ml) was hydrogenated over 10% palladium on charcoal (1.2 g) at 30 p.s.i and 20° C. for 5 hours. The catalyst was filtered off and the filtrate was concentrated under reduced pressure to give 5-amino-2-cyanoindane (10.4 g) which was used directly for the next reaction. A portion, recrystallised from ethanol, formed pinkish needles, m.p. 73°–76° C.

(c) 4-Chloro-3-nitropyridine (11.46 g, 72.8 mmol) was added to a suspension of 5-amino-2-cyanoindane (10.4 g, 65.7 mmol) in ethanol (150 ml) at room temperature. The mixture was stirred overnight at room temperature and then poured into excess ice-cold aqueous ammonia. The yellow solid was filtered off, partially digested in hot ethanol (150 ml), cooled, and re-filtered to give 2-cyano-5-(3-nbitropyrid-4-ylamino)indame (13.61 g, 74%).

(d) b 2-Cyano-5-(3-nitropyrid-4-ylamino)indane (12.46 gm, 44.5 mmol) was suspended in methanol/dichloromethane=1.1 (750 ml) and hydrogenated at 20° C. and 30 p.s.i. over 10% palladium on charcoal (1.25 g) for 2 hours. The catalyst was filtered off and the filtrate was concentrated under reduced pressure to give 5-(3-aminopyrid-4-ylamino)-2-cyanoindane (12.28 g, ca quantitative) as a yellow solid, m.p. 98°–100° C.

(e) A mixture of 5-(3-aminopyrid-4-ylamino)-2-cyanoindane (12.28 g, ca 44.5 mmol from step (d) above), acetic acid (70 ml) and acetic anhydride (70 ml) was heated at reflux under nitrogen for 1.75 hours, cooled, and concentrated under reduced pressure. The residual brown gum was dissolved in 2M hydrochloric acid (40 ml) and washed with ethyl acetate (50 ml). The aqueous layer was rendered basic by the addition of 2M aqueous sodium hydroxide, and the product was extracted into dichloromethane. The combined extracts were wahsed with water (50 ml), dried over magnesium sulphate and the solvent evaporated. The residue was purified by column chromatography on silica gel, eluting with ethyl acetate/methanol (7:1), to give a brown gum, which was recrystallised from ethyl acetate/methanol, to give the 2-cyano-5-(2-methylimidazo[4,5-c]pyrid-1-yl)indane as an off-white powder (9.67 g, 79%), m.p. 174°–176° C. Found: C,74.4; H,5.2; N,20.7. $C_{17}H_{14}N_4$ requires C,74.4; H,5.1; N,20.4%.

(f) A mixture of 2-cyano-5-(2-methylimidazo[4,5-c]pyrid-1-yl)indane (739 mg, 2.70 mmol), 50% aqueous sodium hydroxide (1 ml) and methanol (6 ml) was heated at reflux under nitrogen for 9 hours, cooled, poured onto ice, and the pH of the solution was adjusted to pH 5 by the addition of 2M hydrochloric acid. The resulting precipitate was collected by filtration and dried under vacuum to give the title compound, (426 mg; 54%) as a colourless solid, m.p. 264°–267° C. Found: C,68.9; H,5.1; N,14.1. $C_{17}H_{15}N_3O_2$. 0.2 $H_2O$ requires C,68.8; H,5.2; N,14.1%.

PREPARATION 6

3-(2-Methylimidazo[4,5-c]pyrid-1-yl)benzoic acid a) A solution of ethyl 3-aminobenzoate (3.3 g, 20 mmol) and 4-chloro-3-nitropyridine (3.17 g, 20 mmol) in ethanol (150 ml) was stirred at room temperature for 16 hours and then cooled in an ice-bath. The resulting precipitate was collected, washed with ice-cold ethanol and dried to give ethyl (3-(3-nitro-4-pyridylamino)benzoate hydrochloride (4.17 g) as a yellow crystalline solid, m.p. 201°–204° C. Found: C,5.2; H,4.4; N,12.9. $C_{14}H_{13}N_3O_4$. HCl requires C,51.9; H,4.3; N,13.0%. The mother liquors were evaporated and the residue recrystallised from ethanol to give a further 1.2 g of product.

b) The above product (5.2 g) was partitioned between ethyl acetate and 10% aqueous sodium carbonate solution and the organic layer was washed with water, dried over magnesium sulphate and evaporated. The residue was dissolved in ethanol (300 ml) and the solution was stirred under an atmosphere of hydrogen (40 p.s.i., 2.76 bar) at room temperature in the presence of 5% palladium on charcoal for 16 hours. The mixutre was filtered and the filtrate was evaporated to give ethyl 3-(3-amino-4-pyridylamino)benzoate (4.8 g) as a colourless solid; m.p. 80°–91° C.

c) A solution of the above product (4.8 g) in acetic acid (25 ml) and acetic anhydride (25 ml) was heated under reflux for two hours and evaporated. The residual oil was poured into water, basified with solid sodium carbonate and extracted into ethyl acetate. The combined organic extracts were washed with saturated sodium chloride solution, dired over magnesium sulphate and evaporated. The residue was recrystallised from ethyl acetate to give ethyl 3-(2-methylimidazo[4,5-c]pyrid-1-yl)benzoate (2.9 g) as a colourless solid, m.p.120°–121° C. Found: C,69.1; H,5.4; N,14.8. $C_{15}H_{15}N_3O_2$ requires C,68.3; H,5.3; N,14.9%.

d) A mixture of the above product (1.0 g) and 2M aqueous sodium hydroxide solution (2.2 ml) in ethanol (10 ml) was stirred at room temperature for 18 hours. The ethanol was removed under vacuum and the remaining aqueous solution was neutralised to pH 6 with 2M hydrochloric acid. The resulting precipitate was collected, washed with ice-cold water and diethyl ether and dried to give 3-(2-methylimidazo[4,5-c]pyrid-1-yl)benzoid acid (830 mg) as a colourless powder, m.p. 205°–206° C., which was characterised containing 0.75 equivalents of water. Found: C,62.8; H,4.5; N,15.5.

$C_{13}H_{11}N_3O_2 \cdot 0.75\ H_2O$ requires C,63.0; H,4.7; N,15.7%.

PREPARATION 7

2-(2-Methylimidazo[4,5-c]pyrid-1-yl)benzoic acid a) A solution of ethyl 2-aminobenzoate (3.17 g, 20 mmol) and 4-chloro-3-nitropyridine (2.8 ml) in ethanol (150 ml) was stirred at room temperature for 60 hours. The resulting precipitate was collected, washed with ethanol and dried to give ethyl 2-(3-nitro-4-pyridylamino)benzoate hydrochloride (3.9 g) as a yellow crystalline solid, m.p. 192°–205° C.

The mother liquors were evaporated and the residue was recrystallised from ethanol to give a further 1.5 g of product.

b) The above product (5.3 g) was partitioned between ethyl acetate and 10% aqueous sodium carbonate solution and the organic layer was washed with water, dried over magnesium sulphate and evaporated. The residue was dissolved in ethanol (800 ml) and the solution was stirred under an atmosphere of hydrogen (40 p.s.i., 2.76 bar) at room temperautre in the presence of 5% palladium on charcoal for 16 hours. The mixture was filtered and the filtrate evaporated to give ethyl 2-(3-amino-4-pyridylamino)benzoate (5.1 g) as a colourless oil.

c) A solution of the above product (5.0 g) in acetic acid (25 ml) and acetic anhydride (25 ml) was heated under reflux for 4 hours and evaporated. The residual oil was poured into water, basified with solid sodium carbonate and extracted into ethyl acetate. The combined organic extracts were washed with saturated sodium chloride solution dried over magnesium sulphate and evaporated. The residue was recrystallised from ethyl acetate to give ethyl 2-(2-methylimidazo[4,5-c]pyrid-1-yl)benzoate (3.20 g) as colourless crystals, m.p. 125°–127° C.

d) A mixture of the above product (1.0 g) and 2M aqueous sodium hydroxide solution (2.2 ml) in ethanol (10 ml) was stirred at room temperature for 18 hours. The ethanol was removed under vacuum and the remaining aqueous solution neutralised to pH 6 with 2M hydrochloric acid. The resulting precipitate was collected, washed with ice-cold water and diethyl ether and dried to give 2-(2-methylimidazo[4,6-c]pyrid-1-yl)benzoic acid (760 mg) as a colourless powder, m.p. 181°–183° C. Found: C,63.4; H,4.8; N,15.8. $C_{13}H_{11}N_3O_2 \cdot 0.75$ requires C,63.0; H,4.7; N,15.7%.

PREPARATION 8

5-(2-Methylimidazo[4,5-]pyrid-1-yl)thiophene-2-carboxylic acid a) A solution of 2-cyano-5-nitrothiophene (*Berichte*, 1943, 76B 419; 7.3 g, 47 mmol) in ethanol 150 ml) was hydrogenated at 20 p.s.i. (1.4 bar over 30% palladium on charcoal for 4.5 hours at room temperature. Filtration gave a solution of 2-amino-5-cyanothiophene in ethanol which was used immediately.

b) A solution of the above product (5.8 g, 47 mmol) in ethanol was stirred with 4-chloro-3-nitropyridine (8.89 g, 56 mmol) under nitrogen in the dark for 18 hours. Dichloromethane (100 ml) and thiethylamine (13 ml, 94 mmol) were added, followed by silica (50 g) and the solvent removed under vacuum. The residue was added to a chromatography column, eluting initially with dichloromethane and then with dichloromethane plus 10% ethyl acetate. The product containing fractions were evaporated and the dark red solid was suspended in ethanol (100 ml) and the mixture headed to reflux for 30 minutes. After cooling, the solid was filtered off and dried under vacuum to yield 4-(5-cyanothieny-2-yl)amino-3-nitropyridine 6.1 g, 52%). Found: C,48.77; H,2.42; N,23.37. $C_{10}H_6N_4O_2S$ requires C,48.77; H2.46; N,22.75%.

c) The above product was hydrogenated at 20 p.s.i. (1.4 bar) over 30% palladium on charcoal for 4 hours at room temperature. Filtration and evaporation of the solvent gas 3-amino-4-(5-cyanothien-2-yl)aminopyridine (5.35 g, 100%) which was used immediately in the cyclisation step, following the procedure described in Preparation 2c, to give 2-cyano-5-(2-methylimidazo[4,5-c]pyrid-1-yl)thiophene (2.25 g, 46%). $^1$H NMR (CDCl$_3$), δ=9.10(1H,s), 8.53(1H,d,D=6 Hz), 7.75(1H,d,J=4 Hz), 7.26(1H,d,J=6 Hz), 7.20(1H,d,J=4 Hz), 2.62(3H,s).

d) A solution of 2-cyano-5-(2-methylimidazo[4,5-c]pyrid-1-yl)thiophene (2.7 g, 11 mmol) and sodium hydroxide (1.76 g, 44 mmol) in a mixture of ethanol (23 ml) and water (5 ml) was heated under reflux for 2 hours. The pH was adjusted to 6 with 2N hydrochloric acid and the reaction diluted to 500 ml with water. The solution was divided into two equal portions and each portion was passed through a column of XAD-2 ion-exchange resin (350 g) eluting with water initially, followed by methanol and water (1:1). The product containing fractions were combined and the solvent evaporated under vacuum. The residue was taken up in boiling isopropyl alcohol, filtered and the solvent evaporated under vacuum; azeotroping with toluene yielded the title compound (1.8 g, 63%). $^1$H NMR (DMSOd$_6$), δ=8.91(1H,s), 8.36(1H,d,J=5.5Hz), 7.79(1H,d,J=4.0 Hz), 7.47(1H,d,J=6 Hz), 7.40(1H,d,J=6 Hz), 2.55(3H,s).

We claim:

1. A compound having the formula

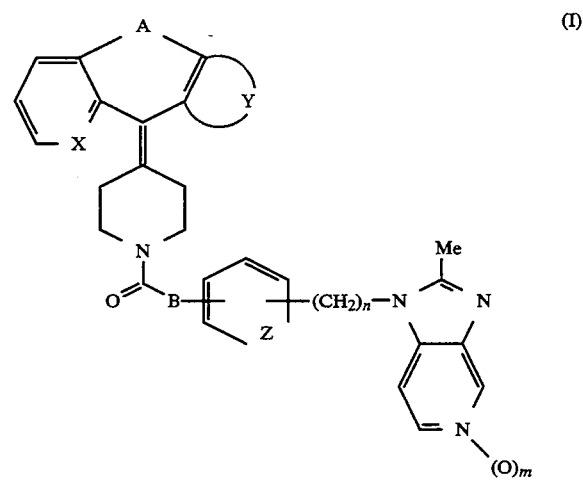

or a pharmaceutically acceptable salt thereof wherein:
X is CH or N;
Z is CH=CH or S;
A is CH$_2$CH$_2$, CH=CH, CH(OH)CH$_2$, or COCH$_2$;
BV is a direct link or —CH$_2$—, —CH(CH$_3$)— or —C(CH$_3$)$_2$—, or when
Z is CH=CH, B may form a cyclopentane ring fused to the attached benzene ring;
Y completes a fused ring which is

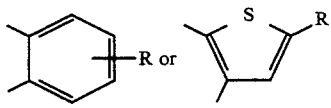

wherein R is H, halo or $C_1$–$C_4$ alkyl;

n is 0, 1 or 2;

and M is 0 or 1.

2. A compound as claimed in claim 1 wherein X is N, Z is CH=CH and Y completes a fused benzene ring of formula:

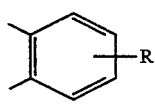

3. A compound as claimed in claim 2 wherein B is a direct link or $CH_2$.

4. A compound as claimed in claim 3 wherein n is 0 and m is 0.

5. A compound as claimed in claim 4 wherein R is Cl, B is a direct link, and A is $CH_2CH_2$.

6. The compound 4-(8-chloro-5,6-dihydro-11H-benzo[5,6]cyclohepta[1,2-b]pyrid-11-ylidene)-1-[4-(2-methylimidazo[4,5-c]pyrid-1-yl)benzoyl]piperidine.

7. A pharmaceutical composition for the treatment of allergic inflammatory conditions in humans comprising an effective amount of a compound of the formula (I), or a pharmaceutically acceptable salt thereof, as claimed in claim 1, together with a pharmaceutically acceptable diluent or carrier.

8. A method of treating allergic rhinitis, sinusitis, asthma, atopic dermatitis or urticaria in a patient in need of such treatment, which comprises administering to said patient an effective amount of a compound of the formula (I) as claimed in claim 1.

* * * * *